(12) United States Patent
Yamaguchi et al.

(10) Patent No.: US 7,973,190 B2
(45) Date of Patent: Jul. 5, 2011

(54) POLYCYCLIC FUSED RING TYPE π-CONJUGATED ORGANIC MATERIAL, INTERMEDIATE THEREFOR, PROCESS FOR PRODUCING POLYCYCLIC FUSED RING TYPE π-CONJUGATED ORGANIC MATERIAL, AND PROCESS FOR PRODUCING INTERMEDIATE OF POLYCYCLIC FUSED RING TYPE π-CONJUGATED ORGANIC MATERIAL

(75) Inventors: Shigehiro Yamaguchi, Nagoya (JP); Caihong Xu, Nagoya (JP)

(73) Assignee: Japan Science and Technology Agency, Saitama (JP)

( * ) Notice: Subject to any disclaimer, the term of this patent is extended or adjusted under 35 U.S.C. 154(b) by 788 days.

(21) Appl. No.: 10/578,352

(22) PCT Filed: Nov. 5, 2004

(86) PCT No.: PCT/JP2004/016433
§ 371 (c)(1),
(2), (4) Date: Dec. 29, 2008

(87) PCT Pub. No.: WO2005/044826
PCT Pub. Date: May 19, 2005

(65) Prior Publication Data
US 2009/0143605 A1 Jun. 4, 2009

(30) Foreign Application Priority Data

Nov. 7, 2003 (JP) .................................. 2003-378923
Jul. 30, 2004 (JP) .................................. 2004-224771

(51) Int. Cl.
*C07F 7/08* (2006.01)
(52) U.S. Cl. ..................... 556/406; 556/431; 556/432
(58) Field of Classification Search .................. 556/406, 556/431, 432
See application file for complete search history.

(56) References Cited

U.S. PATENT DOCUMENTS
2006/0100433 A1 5/2006 Yamaguchi et al.

FOREIGN PATENT DOCUMENTS
EP 0754691 1/1997
(Continued)

OTHER PUBLICATIONS

Yamaguchi et al., {Bis-Silicon-Bridged Stilbene Homologues Synthesized by New Intramolecular Reductive Double Cyclization, Journal of the American Chemical Society (2003), 125(45), 13662-13663.*

(Continued)

*Primary Examiner* — Porfirio Nazario Gonzalez
(74) *Attorney, Agent, or Firm* — Harness, Dickey & Pierce, P.L.C.

(57) ABSTRACT

A polycyclic fused ring type π-conjugated organic material (VIIa, VIIb, VIIc, VIId) is obtained in the following manner. That is, as shown in Scheme 1 below, a starting material (I) is dimetalated with an organometallic base. The starting material (I) thus dimetalated is trapped with an organosilicon reagent (i: (1) n-BuLi or t-BuLi; (2) HMe₂SiCl). As a result, an intermediate is obtained. Thereafter, the intermediate is allowed to react with a metal reductant. This causes an intramolecular reductive cyclization reaction to proceed. As a result, a dianion intermediate is produced. The dianion intermediate is trapped with an electrophile (ii: (1) LiNaph, THF, rt, 5 min; (2) electrophile or NH₄Cl) In this way, the polycyclic fused ring type π-conjugated organic material is obtained. The polycyclic fused ring type π-conjugated organic material, an intermediate therefor, a method for producing the polycyclic fused ring type π-conjugated organic material, and a method for producing the intermediate make it possible to provide a polycyclic fused ring type π-conjugated organic material having excellent light-emitting and charge-transporting properties.

3 Claims, 1 Drawing Sheet

FOREIGN PATENT DOCUMENTS

| | | |
|---|---|---|
| JP | 2006/0100433 | 11/2009 |
| WO | 2004/018488 | 8/2003 |

OTHER PUBLICATIONS

Xu et al. {General Silaindene Synthesis Based on Intramolecular Reductive Cyclization toward New Fluorescent Silicon-Containing_-Electron Materials, Organic Letters, 2004, vol. 6, No. 21, 3707-3710}.*

Japanese Office Action dated Mar. 16, 2010 in corresponding Japanese Application No. 2004-224771, with English translation.

Seok-Bong Choi et al., "A novel α,ω silyl dianionic salt. The synthesis and characterization of remotely connected benzannulated silole monoanions", J. Chem. Soc., Dalton Trans., pp. 841-844 (2000).

International Search Report (PCT/ISA/210).

Maerkl, G. et al. Silaindene—eine einfache Synthese. Tetrahedron Letters, 1992, vol. 33, No. 12, p. 1601-1604.

Yamaguchi, Shigehiro et al. Bis-Silicon-Bridged Stilbene Homologues Synthesized by New Intramolecular Reductive Double Cyclization, Journal of the American Chemical Society, 2003, vol. 125 No. 45, p. 13662-13663.

M. Serby, S. Ijadi-Maghsoodi, and T.J. Barton. "Synthesis and Chemistry of a Trisiladibenzo-Cyclodiyne". XXXIIIrd Symposium on Organosilicon Chemistry, Abstract No. PA-35, Apr. 6-8, 2000, Saginaw, Michigan, USA.

European Office Action dated Jul. 21, 2009.

* cited by examiner

POLYCYCLIC FUSED RING TYPE π-CONJUGATED ORGANIC MATERIAL, INTERMEDIATE THEREFOR, PROCESS FOR PRODUCING POLYCYCLIC FUSED RING TYPE π-CONJUGATED ORGANIC MATERIAL, AND PROCESS FOR PRODUCING INTERMEDIATE OF POLYCYCLIC FUSED RING TYPE π-CONJUGATED ORGANIC MATERIAL

PRIORITY STATEMENT

This application is a national phase entry under 35 U.S.C. §371 of International Application No. PCT/JP2004/016433, filed Nov. 5, 2004, which claims priority under 35 U.S.C. §119 to JP 2003-378923, filed Nov. 7, 2003, and JP 2004-224771, filed Jul. 30, 2004, the entire contents of each of which is incorporated herein in by reference.

TECHNICAL FIELD

The present invention relates to (i) a polycyclic fused ring type α-conjugated organic material which can be applied to an organic electroluminescence (EL) element and which has highly efficient light-emitting and charge-transporting properties, (ii) an intermediate therefor, (iii) a method (process) for producing the polycyclic fused ring type π-conjugated organic material, and (iv) a method (process) for producing the intermediate.

BACKGROUND ART

Conventionally, a display device using an electroluminescence (EL) element makes it possible to attain lower power consumption and thinner thickness, and therefore has been variously studied. Further, the EL element made of an organic material makes it easy to attain lighter weight and larger size, and therefore has been vigorously studied.

Particularly, vigorous studies have been thus far conducted for the purpose of developing (i) an organic material which has a property of emitting light having a color such as blue, which is one of the three primary colors, and (ii) an organic material which has a capability of transporting charges such as holes and electrons (i.e., has a possibility of serving as a semiconductor or a superconductor), regardless of whether such an organic material is a polymer compound or a low-molecular compound.

(Non-patent Document 1) M. Serby, S. Ijadi-Maghsoodi, and T. J. Barton, XXXIIIrd Symposium on Organosilicon Chemistry, Abstract No. PA-35, Apr. 6-8, 2000, Saginaw, Mich., USA.

DISCLOSURE OF INVENTION

Problems to be Solved by the Invention

However, there are still only a few organic materials having really excellent properties in terms of color purity, light-emitting efficiency, carrier mobility, and carrier injection. In this filed, it is currently one of the tasks of highest priority to develop such a material.

The present invention has been made in view of the foregoing problems. It is an object of the present invention to provide (i) a novel polycyclic fused ring type π-conjugated organic material which exhibits excellent properties and which can be applied to a light-emitting material or charge-transporting material used for an organic electroluminescence (EL) element, (ii) an intermediate therefor, (iii) a method for producing the polycyclic fused ring type π-conjugated organic material, and (iv) a method for producing the intermediate.

The inventors of the present invention studied diligently in order to attain the foregoing object. As a result, the inventors found novel compounds respectively having structures represented by following formulas (1) through (3) and methods for producing the compounds, and found that the compounds exhibit good light-emitting properties. Based on these finding, the inventors have accomplished the present invention.

Means to Solve the Problems

In order to solve the foregoing problems, a polycyclic fused ring type π-conjugated organic material according to the present invention has a structure represented by following formula (1):

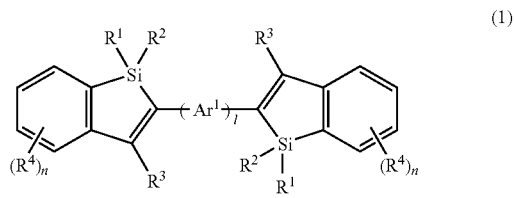

(1)

The polycyclic fused ring type π-conjugated organic material may have a structure represented by following formula (2):

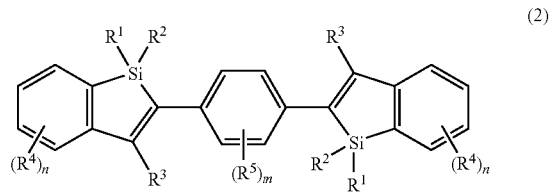

(2)

In order to solve the foregoing problems, another polycyclic fused ring type π-conjugated organic material according to the present invention has a structure represented by following formula (3):

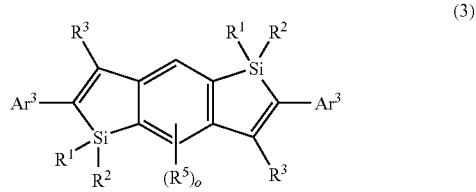

(3)

The polycyclic fused ring type π-conjugated organic material may have a structure represented by following formula (4):

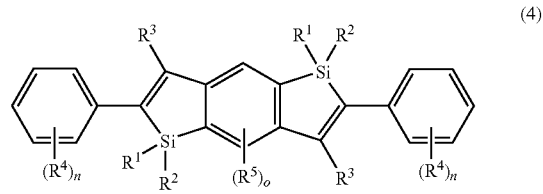

(4)

In order to solve the foregoing problems, an intermediate according to the present invention for synthesis of a polycyclic fused ring type π-conjugated organic material has a structure represented by following formula (5):

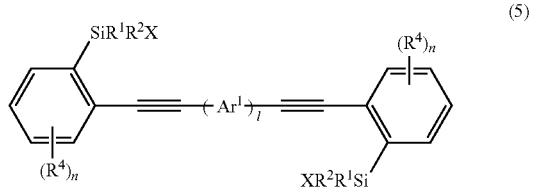
(5)

The intermediate may have a structure represented by following formula (6):

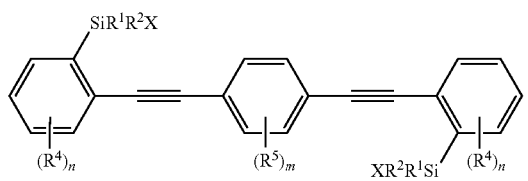
(6)

In order to solve the foregoing problems, another intermediate according to the present invention for synthesis of a polycyclic fused ring type π-conjugated organic material has a structure represented by following formula (7):

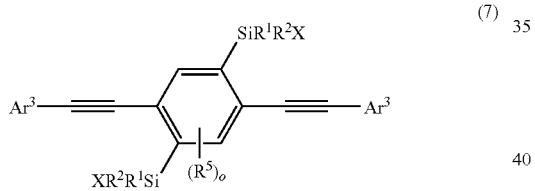
(7)

The intermediate may have a structure represented by following formula (8):

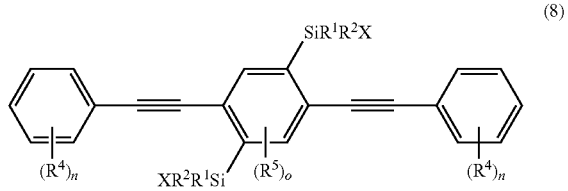
(8)

A method according to the present invention for producing a polycyclic fused ring type π-conjugated organic material includes the steps of: producing a dianion intermediate by allowing the intermediate described above in formula (5) to react with a metal reductant; and obtaining the polycyclic fused ring type π-conjugated organic material described above in formula (1) by trapping the dianion intermediate by using an electrophile.

Another method according to the present invention for producing a polycyclic fused ring type π-conjugated organic material includes the steps of: producing a dianion intermediate by allowing the intermediate described above in formula (7) to react with a metal reductant; and obtaining the polycyclic fused ring type π-conjugated organic material described above in formula (3) by trapping the dianion intermediate by using an electrophile.

A method according to the present invention for producing an intermediate for synthesis of a polycyclic fused ring type n-conjugated organic material includes the steps of: dimetalating, by using an organometallic base, a material having a structure represented by following formula (9); and producing the intermediate described above in formula (5) by trapping, by using an organosilicon reagent, the material thus dimetalated.

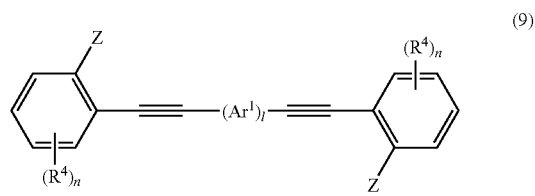
(9)

Another method according to the present invention for producing an intermediate for synthesis of a polycyclic fused ring type π-conjugated organic material includes the steps of: dimetalating, by using an organometallic base, a material having a structure represented by following formula (10); and producing the intermediate described above in formula (7) by trapping, by using an organosilicon reagent, the material thus dimetalated.

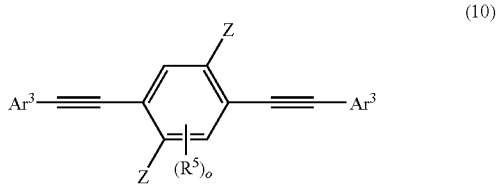
(10)

In order to solve the foregoing problems, another polycyclic fused ring type π-conjugated organic material has a structure represented by following formula (11):

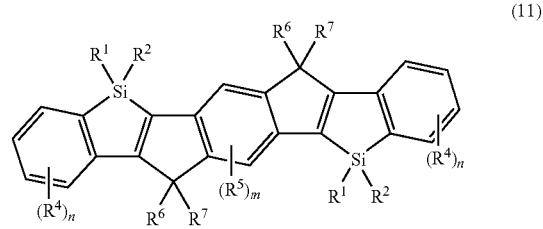
(11)

In order to solve the foregoing problems, another polycyclic fused ring type π-conjugated organic material has a structure represented by following formula (12):

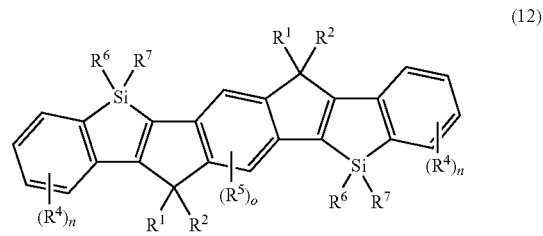
(12)

In order to solve the foregoing problems, another intermediate according to the present invention for synthesis of a polycyclic fused ring type π-conjugated organic material has a structure represented by following formula (13):

(13)

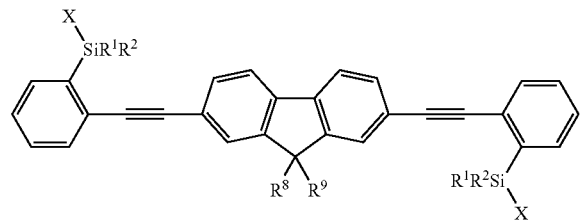

In order to solve the foregoing problems, another polycyclic fused ring type π-conjugated organic material has a structure represented by following formula (14):

(14)

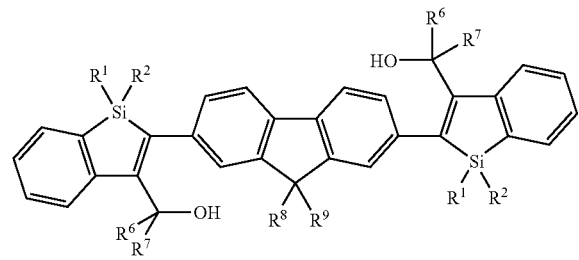

In order to solve the foregoing problems, another polycyclic fused ring type π-conjugated organic material has a structure represented by following formula (15):

(15)

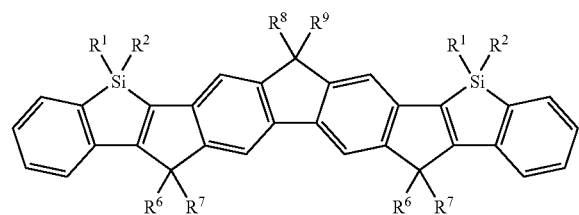

In order to solve the foregoing problems, another intermediate according to the present invention for synthesis of a polycyclic fused ring type π-conjugated organic material has a structure represented by following formula (16):

(16)

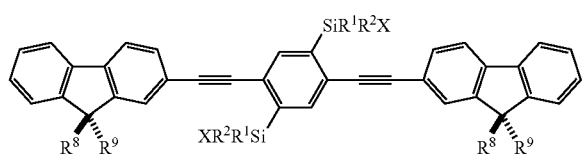

In order to solve the foregoing problems, another polycyclic fused ring type π-conjugated organic material has a structure represented by following formula (17):

(17)

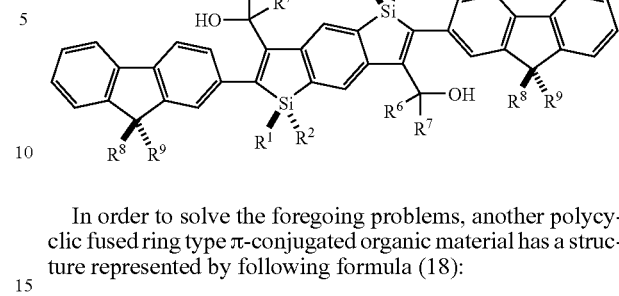

In order to solve the foregoing problems, another polycyclic fused ring type π-conjugated organic material has a structure represented by following formula (18):

(18)

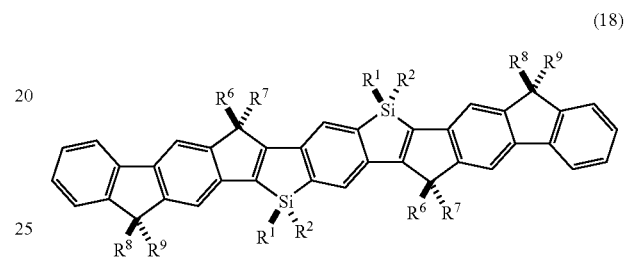

The meanings of the symbols used in any one of formulas (1) through (18) are as follows.

$Ar^1$ is an arylene group, a substituted arylene group, an oligoarylene group, a substituted oligoarylene group, a bivalent heterocyclic group, a bivalent substituted heterocyclic group, a bivalent oligoheterocyclic group, or a bivalent substituted oligoheterocyclic group.

$Ar^3$ is an aryl group, a substituted aryl group, a monovalent oligoarylene group, a monovalent substituted oligoarylene group, a monovalent heterocyclic group, a monovalent substituted heterocyclic group, a monovalent oligoheterocyclic group, or a monovalent substituted oligoheterocyclic group.

$R^1$ and $R^2$ are independently a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amino group, a substituted amino group, a silyl group, a substituted silyl group, a silyloxy group, a substituted silyloxy group, an arylsulfonyloxy group, an alkylsulfonyloxy group, a monovalent heterocyclic group, or a halogen atom.

$R^3$ is a hydrogen group, an alkyl group, an alkylthio group, an aryl group, an arylthio group, an arylalkyl group, an arylalkylthio group, an arylalkenyl group, an arylalkynyl group, an allyl group, a hydroxyalkyl group, a hydroxymethyl group, a substituted hydroxymethyl group, a silyl group, a substituted silyl group, a stannyl group, a substituted stannyl group, magnesium halide, zinc halide, boronic acid, boronic ester, a boryl group, a monovalent heterocyclic group, or a halogen atom.

$R^4$ and $R^5$ are independently a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amino group, a substituted amino group, a silyl group, a substituted silyl group, a silyloxy group, a substituted silyloxy group, an arylsulfonyloxy group, an alkylsulfonyloxy group, a boryl group, a substituted boryl group, a monovalent heterocyclic group, or a halogen atom.

$R^6$ and $R^7$ are either (i) independently a hydrogen atom, an alkyl group, an aryl group, a monovalent heterocyclic group, an alkoxy group, an aryloxy group, an arylalkyl group, an arylalkoxy group, an arylalkenyl group, an arylalkynyl group, or an allyl group, or (ii) mutually a bivalent biaryl group.

$R^8$ and $R^9$ are either (a) independently a hydrogen atom, an alkyl group, an alkoxy group, an alkylthio group, an aryl group, a substituted aryl group, an arylalkyl group, an arylalkenyl group, an arylalkynyl group, an allyl group, a silyl group, a substituted silyl group, an acyl group, or a monovalent heterocyclic group, or (b) mutually a bivalent biaryl group.

l is an integer of 0 or 1. n and m are independently an integer of 0 to 4. o is an integer of 0 to 2. However, n is an integer of 0 to 5 in formulas (4) and (8).

X is a hydrogen atom, a halogen atom, an alkoxy group, an alkylthio group, an aryloxy group, an arylthio group, a silyl group, a substituted silyl group, a stannyl group, a substituted stannyl group, a silyloxy group, a substituted silyloxy group, an arylsulfonyloxy group, or an alkylsulfonyloxy group. Z is a bromine atom or an iodine atom.

Effects of the Invention

An example of the designing of a material capable of exhibiting good light-emitting and charge-transporting properties is to build a molecular having a highly planar π-conjugated skeleton. For example, the inventors of the present invention has found a method for synthesizing a compound having, as a basic structure, the following planar silicon cross-linked stillbene skeleton in which trans-stillbene skeletons are cross-linked by substituted silicon groups.

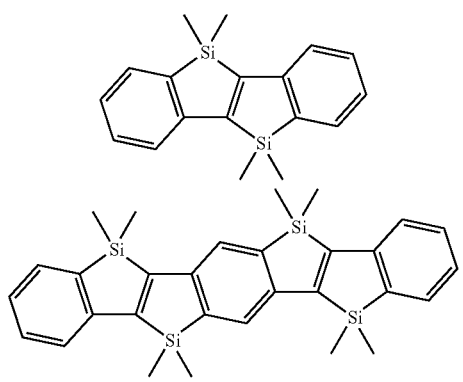

Silicon Cross-Linked Stillbene and a Derivative Thereof

Furthermore, the inventors have found polycyclic fused ring type π-conjugated organic materials respectively represented by formulas (1) through (3) shown above. Each of the materials contains organic silicon, and is a compound which is given flexibility in structure modification but which retains the characteristics of the skeleton, e.g., good light-emitting properties and the like.

The compound as such can be used as a high-performance electronic material such as a highly efficient light-emitting organic material or charge-transporting material. In addition, the compound is expected to useful as a novel constitutional unit of a polymer.

An example of the compound containing organic silicon is 5,5,10,10-tetramethyl-5,10-disila-5,10-dihydroindeno[2,1-a]inden, which is known to be obtained by a synthetic method shown in Non-patent Document 1.

However, the synthetic method makes use of a special high-temperature thermal decomposition reaction. Therefore, the synthetic method has the following fatal restrictions (1) through (3) in terms of synthesis: (1) the method is not suitable for mass synthesis; (2) the method is not suitable to synthesis of a derivative having a functional group necessary for synthesis of a polymer; (3) the method cannot be applied to synthesis of a polycyclic fused ring type compound.

Therefore, there has been no effective method for synthesizing the compounds, i.e., the polycyclic fused ring type π-conjugated organic materials containing organic silicon.

In order to overcome the foregoing problems, the inventors made an effort to develop a conceptually novel method for, producing organic materials respectively represented by formulas (1) through (4) shown above. As a result, the inventors have come up with a producing method of the present invention. The producing method shown in the present invention makes use of an intramolecular reductive cyclization reaction, and is the first effective general method for producing a polycyclic fused ring type π-conjugated organic material having a silainden skeleton as a basic structure.

BEST MODE FOR CARRYING OUT THE INVENTION

Figure 1:
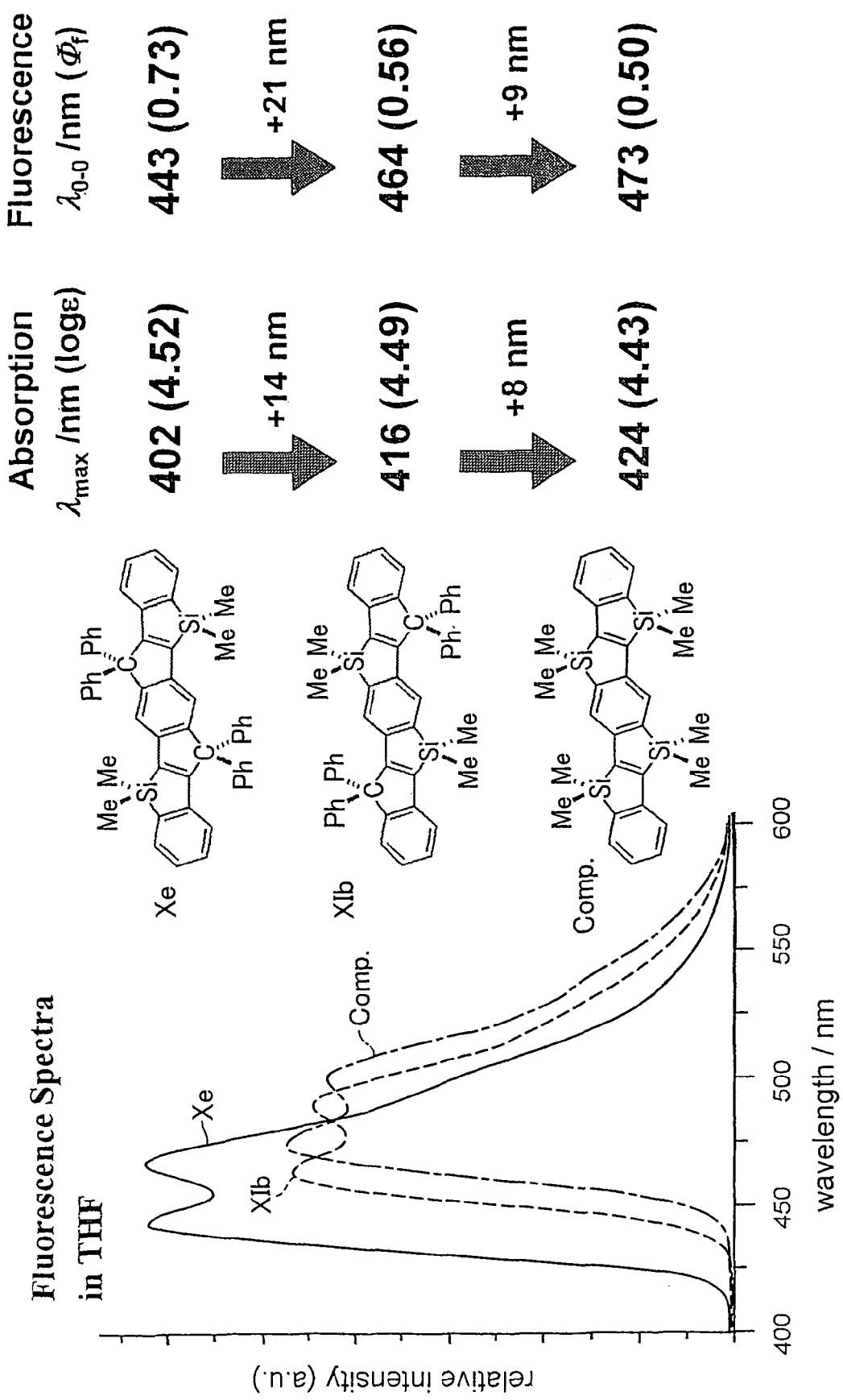
FIG. 1 is a graph showing results of examining: (a) wavelengths at which (i) Targeted Compound Xe, which is a fused ring type π-conjugated organic material according to the present invention, (ii) Targeted Compound Xib, which is another fused ring type π-conjugated organic material according to the present invention, and (iii) Comparative Compound Comp., which is used for comparison with the two targeted compounds, exhibit absorption maximums, respectively; and (b) respective fluorescence properties of the three compounds.

An embodiment of the present invention will be described below.

A polycyclic fused ring type π-conjugated organic material according to the present invention is obtained in the following manner. That is, as shown in the following formulas, a starting material is dimetalated by using an organometallic base. The starting material thus dimetalated is trapped by using an organosilicon reagent. As a result, an intermediate is obtained. Thereafter, the intermediate is allowed to react with a metal reductant. This causes an intramolecular reductive cyclization reaction. As a result, a dianion intermediate is produced. Thereafter, the dianion intermediate is trapped by using an electrophile. In this way, the fused ring type π-conjugated organic material according to the present invention is obtained.

First, the following explains methods for synthesizing intermediates represented by following formula (5) and (7), respectively.

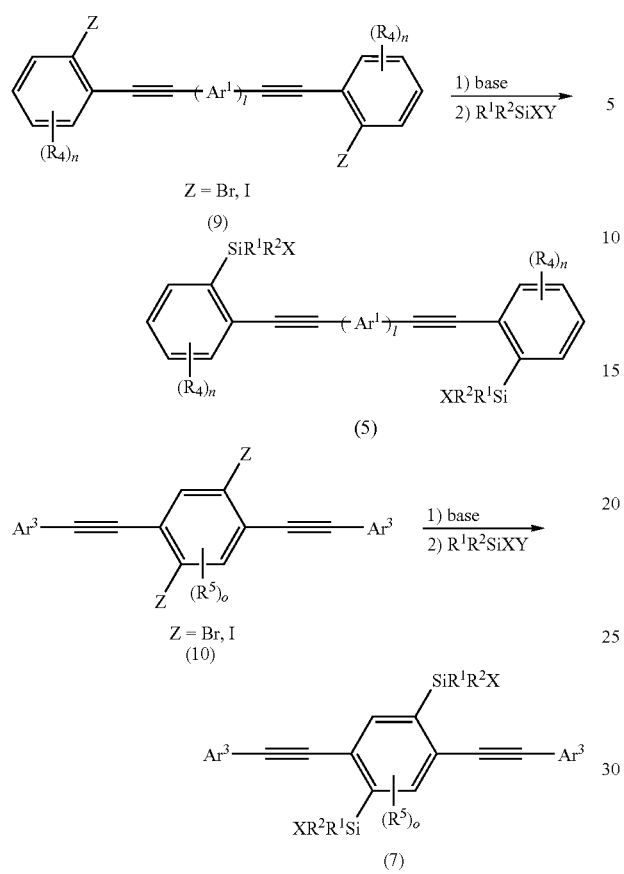

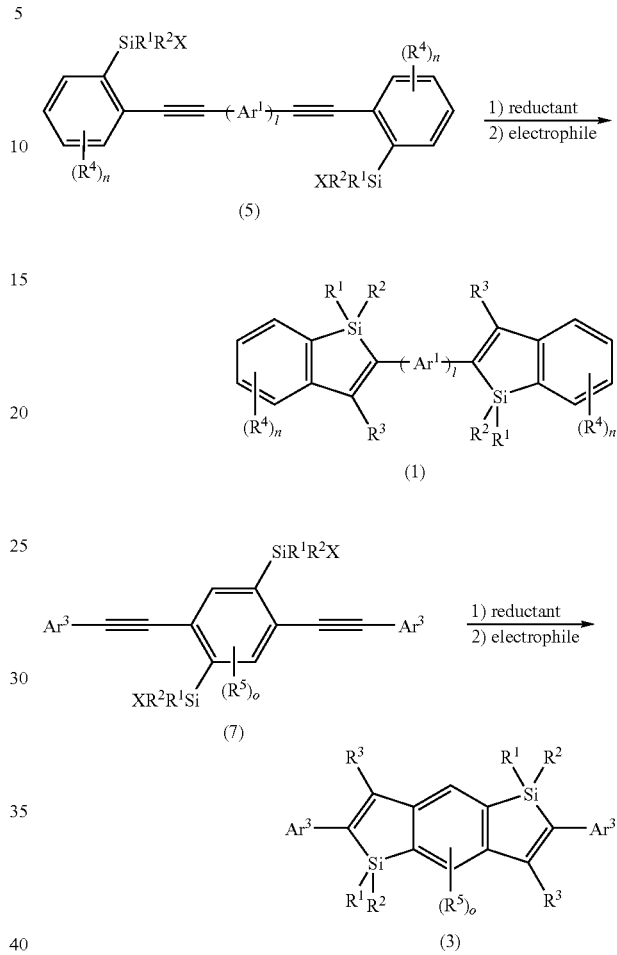

Each of the materials respectively represented by formulas (9) or (10) is dimetalated by a halogen-metal exchange reaction using an organometallic base. Thereafter, the material thus dimetalated is trapped by using an organosilicon reagent represented by general formula $R^1R^2SiXY$. As a result, the intermediate represented by formulas (5) or (7) can be synthesized.

Examples of the organometallic base used herein include: (i) an organolithium reagent such as n-BuLi, s-BuLi, or t-BuLi; (ii) an organomagnesium reagent such as an alkyl Grignard reagent or alkylmagnesium amide; and (iii) an alkyl zinc reagent. Metalation in THF using t-BuLi gives the highest yield.

Further, in the organosilicon reagent $R^1R^2SiXY$, X and Y are independently a hydrogen atom, a halogen atom, an alkoxy group, an alkylthio group, an aryloxy group, an arylthio group, a silyl group, a substituted silyl group, a silyloxy group, a substituted silyloxy group, an arylsulfonyloxy group, an alkylsulfonyloxy group, a stannyl group, or a substituted stannyl group.

In formulas (5) and (7), it is particularly advantageous that X is a hydrogen atom or an alkoxy group. In the synthesis of a compound having a hydrogen atom as X, it is possible to use $R^1R^2SiH_2$, or $R^1R^2SiHCl$, as the organosilicon reagent $R^1R^2SiXY$.

In the synthesis of a compound having an alkoxy group as X, it is possible to use $R^1R^2Si(OR)_2$ or $R^1R^2SiCl(NR_2)$ as the organosilicon reagent $R^1R^2SiXY$. In a case where $R^1R^2SiCl(NR_2)$ is used, a targeted product can be obtained by allowing the dimetalated starting material to react with $R^1R^2SiCl(NR_2)$ and subsequently, without isolating the product of the reaction, performing alkoholysis of the product of the reaction in the presence of an acid catalyst such as ammonium chloride.

The following explains the intramolecular reductive cyclization reaction in accordance with the above reaction formulas. the compound represented by formula (5) or (7) is allowed to react with a metal reductant. This causes an intramolecular reductive cyclization reaction to proceed. As a result, a dianion intermediate is produced. The dianion intermediate is trapped with an electrophile. As a result, the cyclized product represented by formula (1) or (3) is obtained as a polycyclic fused ring type rt-conjugated organic material according to the present invention.

Examples of the metal reductant used herein include lithium, lithium-naphthalenide, lithium-biphenylide, lithium (4,4'-di-tert-butylbiphenylide), lithium[8-(N,N-dimethylamino)naphthalenide], lithium/liquefied ammonium, sodium, sodium-naphthalenide, sodium-biphenylide, sodium (4,4-di-tert-butylbiphenylide), sodium[8-(N,N-dimethylamino)naphthalenide], sodium/liquefied ammonium, potassium, potassium graphite, and the like.

Examples of the solvent used for the reaction include (i) THF and (ii) an ether solvent such as diethylether, dimethylether, or 1,2-dimetoxyethane. The reaction temperature may be within a range of from −78° C. to 5° C., preferably within a range of from −20° C. to 30° C.

The reaction has following characteristics (1) and (2): (1) a dianion intermediate is produced; and (2) various substituents $R^3$ can be introduced by using various electrophiles. Typical examples of the electrophile include: (i) a normal carbon electrophile such as alkyl halide or a carbonyl compound; (ii) an electrophilic halogenating agent such as $ICH_2CH_2I$, $I_2$, $Br_2$, $IC_1$, NIS, NBS, $BrCH_2CH_2Br$, $BrCl_2CCCl_2Br$, or $BrF_2CCF_2Br$; and (iii) an electrophilic metalating agent such as $Me_3SnCl$, $Bu_3SnCl$, $Ph_3SnCl$, $R_3SiCl$, $R_2Si(OR)Cl$, $RSi(OR)_2Cl$, $Si(OR)_3Cl$, $R_2SiF_2$, $RSiF_3$, $B(OR)_3$, $(iPrO)B(—OCMe_2CMe_2O—)$, $ClB(NR_2)_2$, $MgCl_2$, $MgBr_2$, $MgI_2$, $ZnCl_2$, $ZnBr_2$, $ZnI_2$, or $ZnCl_2(tmen)$ (provided that R is an alkyl group or an aryl group). Further, the use of a fluorine compound such as aryl fluoride allows the direct introduction of an aryl group, a heterocyclic group, or a fluorine-substituted alkyl group.

As shown in the following reaction formulas, formulas (2'), (4'), (14), and (17) can be converted to formulas (11), (12), (15), and (18), respectively, by using a normal Lewis acid such as $BF_3.OEt_2$, $BAr_3$, $AlCl_3$, $AlBr_3$, $EtAlCl_2$, or $Et_2AlCl$.

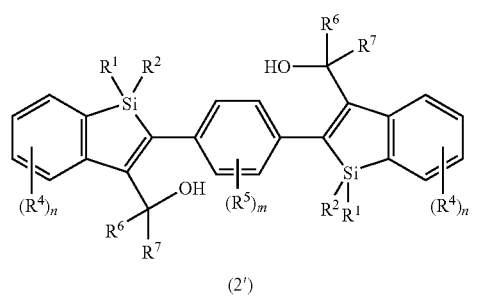

(2')

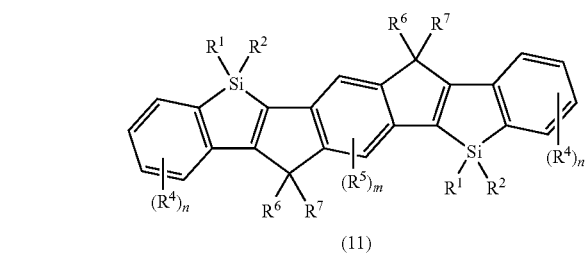

(11)

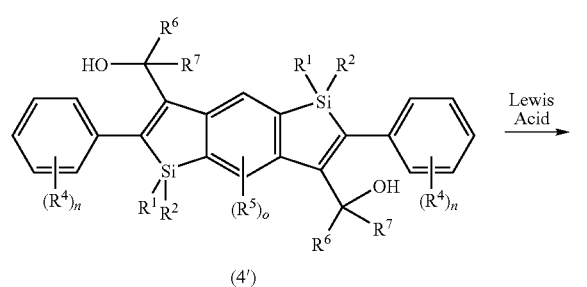

(12)

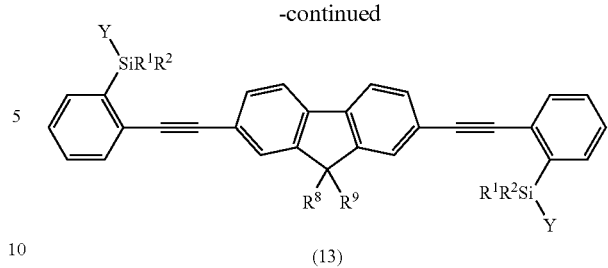

(13)

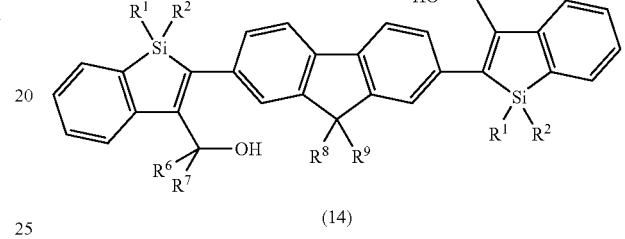

(14)

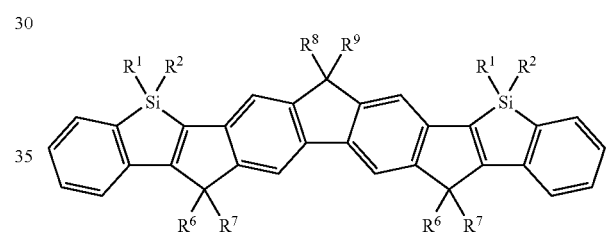

(15)

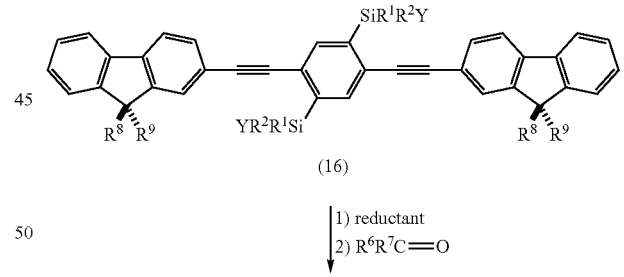

(16)

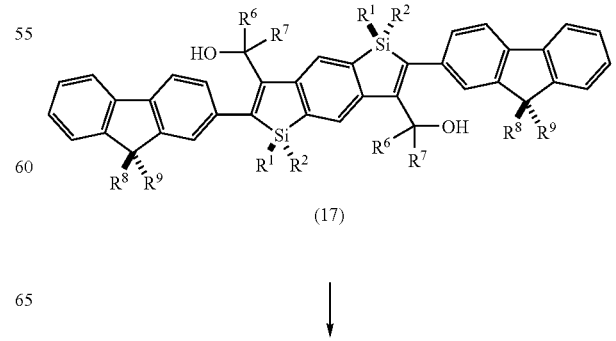

(17)

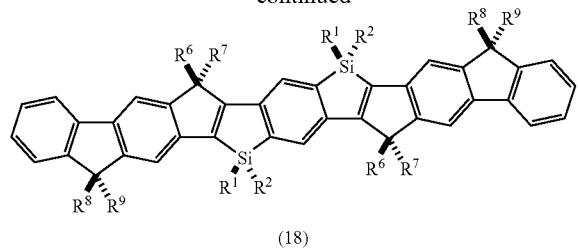

(18)

EXAMPLES

In the following, Examples will be described, by which the present invention will be described more specifically. It should be noted that the present invention is not limited to these Examples.

Example 1

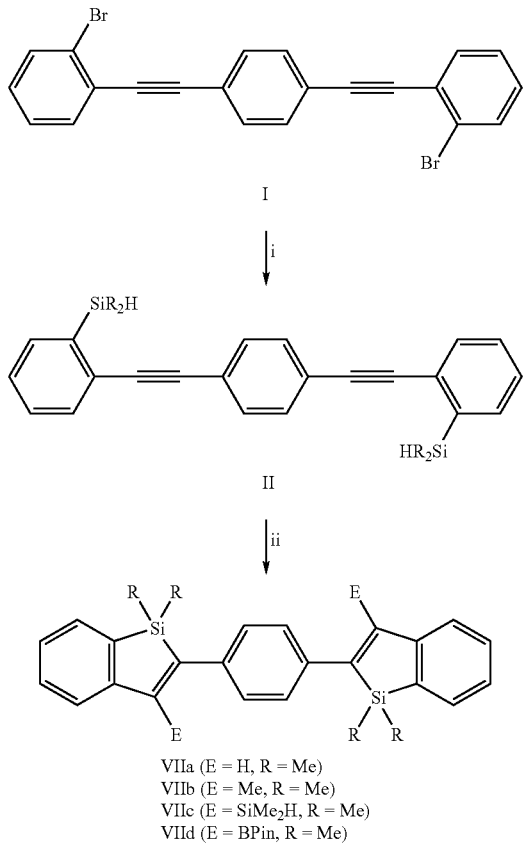

VIIa (E = H, R = Me)
VIIb (E = Me, R = Me)
VIIc (E = SiMe$_2$H, R = Me)
VIId (E = BPin, R = Me)

In the following, a method for synthesizing Intermediate (II) (i.e., 1,4-Bis[(2-dimethylsilylphenyl)ethynyl]benzene) will be described with reference to Scheme 1 shown above. First, to a solution in which 1,4-Bis[(2-bromophenyl)ethynyl]benzene (I) (7.01 g, 16.07 mmol) was mixed with THF (150 mL), a pentane solution of tert-butyllithium (1.44 M, 46.0 mL, 66.24 mmol) was added dropwise at −78° C. The reaction mixture was stirred for 1 hour at the same temperature. Thereafter, to the reaction mixture, chlorodimethylsilane (7.4 mL, 66.63 mmol) was added using a syringe. Then, the reaction mixture was stirred for 22 hours while the temperature was allowed to slowly rise to room temperature.

Thereafter, the solvent was distilled off under reduced pressure. To the resulting product, ether was added. The insoluble was filtered out. The filtrate was concentrated, and was then separated and purified by silica gel column chromatography (developing solvent: hexane/ethyl acetate, 100/1, Rf=0.38). As a result, targeted Intermediate (II) was obtained (6.06 g, 15.35 mmol) in a 96% yield.

The properties of Intermediate (II) are as follows. $^1$H NMR (CDCl$_3$): δ 0.48 (d, J=3.9 Hz, 12H), 4.65 (m, J=2.7 Hz, 2H), 7.37 (m, 4H), 7.54 (s, 4H), 7.58 (m, 4H). $^{13}$C NMR (CDCl$_3$): δ −3.87, 91.88, 92.12, 123.24, 127.76, 128.48, 129.23, 131.32, 131.93, 137.74, 140.19.

Note the symbols i and ii respectively put beside the downward arrows which indicates the reactions and which are shown in Scheme 1. The symbols i and ii indicate abbreviations for solvents and reaction conditions. Specifically, the symbol i indicates (1) n-BuLi or t-BuLi and (2) NMe$_2$SiCl, and the symbol ii indicates (1) LiNaph, THF, 5 minutes at room temperature (rt) and (2) electrophile or NH$_4$Cl. These abbreviations apply to Schemes 2 and 3 shown below.

Example 2

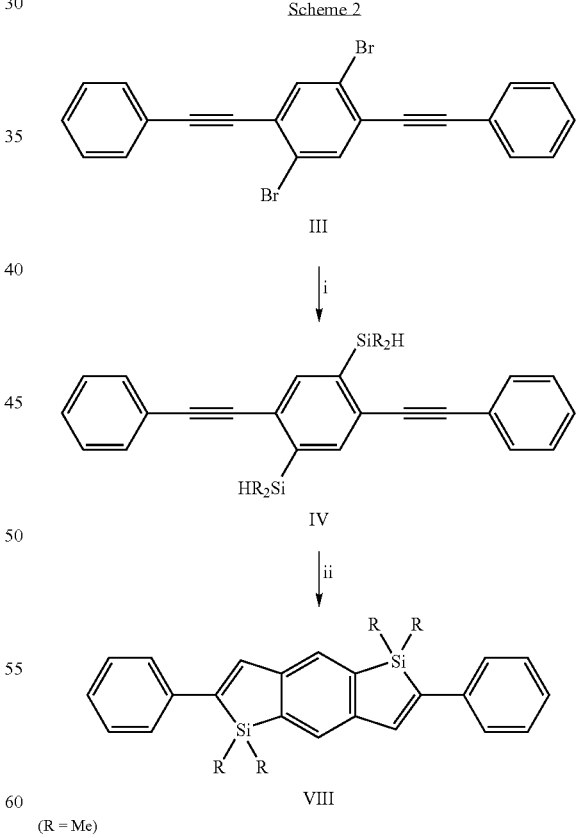

(R = Me)

In the following, a method for synthesizing Intermediate (IV) (i.e., 1,4-Bis(phenylethynyl)-2,5-bis(dimethylsilyl)benzene) will be described with reference to Scheme 2 shown above. First, to a solution in which 2,5-Bis(phenylethynyl)-

1,4-dibromobenzene (III) g, 2.29 mmol) was mixed with THF (20 mL), a pentane solution of tert-butyllithium (1.45 M, 6.4 mL, 9.28 mmol) was added dropwise at −78° C. The reaction mixture was stirred for 1 hour at the same temperature. Thereafter, to the reaction mixture, chlorodimethylsilane (7.4 mL, 66.63 mmol) was added using a syringe. Then, the reaction mixture was stirred for 8 hours while the temperature was allowed to slowly rise to room temperature.

Thereafter, the solvent was distilled off under reduced pressure. To the resulting product, ether was added. The insoluble was filtered out. The filtrate was concentrated, and was then separated and purified by silica gel column chromatography (developing solvent: hexane/ethyl acetate, 100/1, Rf=0.50). As a result, targeted Intermediate (IV) was obtained (0.75 g, 1.90 mmol) in an 83% yield.

The properties of Intermediate (IV) are as follows. $^1$H NMR (CDCl$_3$): δ 0.48 (d, J=3.6 Hz, 12H), 4.63 (m, J=3.6 Hz, 2H), 7.37 (m, 6H), 7.55 (m, 4H), 7.73 (s, 2H).

Example 3

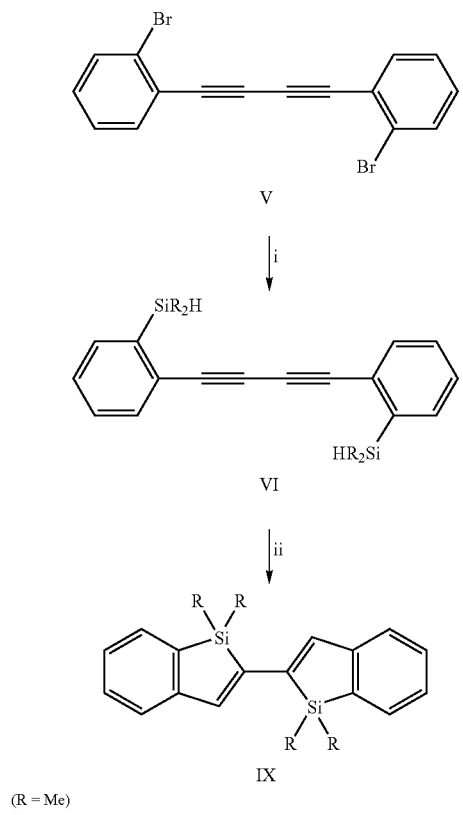

Scheme 3

(R = Me)

In the following, a method for synthesizing Intermediate (VI) (i.e., 1,4-Bis(2-dimethylsilylphenyl)-1,3-butadiyne) will be described with reference to Scheme 3 shown above. First, to a solution in which 1,4-Bis(2-bromophenyl)-1,3-butadiyne (7.00 g, 19.44 mmol) was mixed with ether (195 mL), a hexane solution of n-butyllithium (1.6 M, 26.0 mL, 41.6 mmol) was added dropwise at −78° C. The reaction mixture was stirred for 1.5 hour at the same temperature. Thereafter, to the reaction mixture, chlorodimethylsilane (5.5 mL, 49.57 mmol) was added using a syringe. Then, the reaction mixture was stirred for 6 hours while the temperature was allowed to slowly rise to room temperature. Thereafter, the solvent was distilled off under reduced pressure. The mixture so obtained was separated and purified by silica gel column chromatography (developing solvent: hexane, Rf=0.53). As a result, targeted Intermediate (VI) was obtained (5.50 g, 17.26 mmol, 89% yield) in the form of a light yellow liquid.

The properties of Intermediate (VI) are as follows. $^1$H NMR (CDCl$_3$): δ 0.45 (d, J=3.9 Hz, 12H), 4.56 (m, J=3.6 Hz, 2H), 7.35 (m, 4H), 7.56 (m, 4H).

Example 4

In the following, a method for synthesizing 1,4-Bis(1,1-dimethyl-1H-1-silainden-2-yl)benzene (VIIa) will be described with reference to Scheme 1 shown above. First, a mixture of lithium (28 mg, 4.03 mmol) and naphthalene (519 mg, 4.05 mmol) was stirred in THF (4.5 mL) at room temperature for 4 hours. As a result, a lithium-naphthalenide solution was prepared. To the solution, a solution in which Intermediate (II) (396 mg, 1.00 mmol) was mixed with THF (2 mL) was added at room temperature. Immediately after the reaction mixture had been stirred for 5 minutes, a saturated ammonium chloride solution was added to the reaction mixture. Then, the reaction mixture was extracted with ether.

The organic solvent layer so obtained was washed with saturated saline, and then was dried using anhydrous MgSO$_4$. Then, the anhydrous MgSO$_4$ was filtered out. Thereafter, the solvent was distilled off under reduced pressure. The mixture so obtained was separated and purified by silica gel column chromatography (developing solvent: CHCl$_3$). As a result, Targeted Compound (VIIa) (205 mg, 0.52 mmol), which is a polycyclic fused ring type π-conjugated organic material of the present invention, was obtained in a 52% yield.

The properties of Targeted Compound (VIIa) are as follows. $^1$H NMR (CDCl$_3$): δ 0.50 (s, 12H), 7.22 (m, 2H), 7.33 (m, 4H), 7.52 (s, 4H), 7.56 (m, 4H). $^{13}$C NMR (CDCl$_3$): δ −3.06, 124.34, 126.64, 126.95, 130.08, 131.73, 137.94, 138.34, 140.82, 144.91, 148.99.

Example 5

In the following, a method for synthesizing 1,4-Bis(1,1,3-trimethyl-1H-1-silainden-2-yl)benzene (VIIb) will be described with reference to Scheme 1 shown above. A mixture of lithium (9 mg, 1.30 mmol) and naphthalene (166 mg, 1.30 mmol) was stirred in THF (2 mL) at room temperature for 4 hours. As a result, a lithium-naphthalenide solution was prepared. To the solution, a solution in which Intermediate (II) (105 mg, 0.26 mmol) was mixed with THF (1 mL) was added at room temperature. Immediately after the reaction mixture had been stirred for 5 minutes, the reaction mixture was cooled down to −78° C. and then mixed with dimethyl sulfate. Then, the reaction mixture was stirred for 4 hours while the temperature was allowed to rise to room temperature.

A saturated ammonium chloride solution was added to the reaction mixture. Thereafter, the reaction mixture extracted with chloroform. The organic solvent layer so obtained was washed with saturated saline, and then was dried using anhydrous MgSO$_4$. Then, the anhydrous MgSO$_4$ was filtered out. Thereafter, the solvent was distilled off under reduced pressure. To the mixture so obtained, hexane was added. Then, the insoluble was collected by filtration. As a result, Targeted Compound (VIIb) (93 mg, 0.22 mmol), which is a polycyclic fused ring type π-conjugated organic material of the present invention, was obtained in an 83% yield.

The properties of Targeted Compound (VIIb) are as follows. $^1$H NMR (CDCl$_3$): δ 0.38 (s, 12H), 2.21 (s, 6H), 7.18 (s, 4H), 7.26 (m, 2H), 7.42 (m, 4H), 7.57 (d, J=7.2 Hz, 2H).

Example 6

In the following, a method for synthesizing 1,4-Bis(1,1-dimethyl-3-dimethylsilyl-1H-1-silainden-2-yl)benzene (VIIc) will be described with reference to Scheme 1 shown above.

Targeted Compound (VIIc) was synthesized in the same manner as Targeted Compound (VIIb), except that dimethylchlorosilane was used instead of dimethyl sulfate as an electrophile. As a result, Targeted Compound (VIIc), which is a polycyclic fused ring type π-conjugated organic material of the present invention, was obtained in an 87% yield.

The properties of Targeted Compound (VIIc) are as follows. $^1$H NMR (CDCl$_3$): δ 0.21 (d, J=3.6 Hz, 12H), 0.35 (s, 12H), 4.38 (m, J=4.0 Hz, 2H), 7.06 (s, 4H), 7.23 (t, J=7.2 Hz, 2H), 7.39 (t, J=7.6 Hz, 2H), 7.60 (t, 4H). $^{13}$C NMR (CDCl$_3$): δ −4.23, −2.63, 124.98, 126.01, 126.73, 129.90, 131.82, 138.28, 140.62, 152.61, 153.80, 163.93.

Example 7

In the following, a method for synthesizing 1,4-Bis[1,1-dimethyl-3-(4,4,5,5-tetramethyl-1,3,2-dioxaborolanyl)-1H-1-silainden-2-yl]benzene (VIId) will be described with reference to Scheme 1 shown above.

Targeted Compound (VIId) was synthesized in the same manner as Targeted Compound (VIIb), except that 1-isopropoxy-4,4,5,5-tetramethyl-1,3,2-dioxaborolane was used instead of dimethyl sulfate as an electrophile. As a result, Targeted Compound (VIId), which is a polycyclic fused ring type π-conjugated organic material of the present invention, was obtained in a 43% yield.

The properties of Targeted Compound (VIId) are as follows. $^1$H NMR (CDCl$_3$): δ 0.36 (s, 12H), 1.30 (s, 24H), 7.18 (t, J=7.2 Hz, 2H), 7.26 (s, 4H), 7.34 (t, J=7.2 Hz, 2H), 7.47 (d, J=7.2 Hz, 2H), 7.52 (d, J=6.8 Hz, 2H). $^{13}$C NMR (CDCl$_3$): δ −3.86, 24.95, 83.93, 124.72, 126.16, 127.10, 130.00, 131.67, 138.20, 140.09, 151.58, 158.89. $^{29}$Si NMR (CDCl$_3$): δ 5.20

Example 8

In the following, a method for synthesizing 1,1,5,5-Tetramethyl-2,6-diphenyl-1,5-dihydro-1,5-disila-s-indacene (VIII) will be described with reference to Scheme 2 shown above.

A mixture of lithium (15.2 mg, 2.19 mmol) and naphthalene (280.2 mg, 2.19 mmol) was stirred in THF (2 mL) at room temperature for 4 hours. As a result, a lithium-naphthalenide solution was prepared. To the solution, a solution in which Compound (IV) (200.0 mg, 0.51 mmol) was mixed with THF (1.5 mL) was added at room temperature.

Immediately after the reaction mixture had been stirred for 5 minutes, a saturated ammonium chloride solution was added to the reaction mixture. Then, the reaction mixture was extracted with ether. The organic solvent layer so obtained was washed with saturated saline, and then was dried using anhydrous MgSO$_4$. Then, the anhydrous MgSO$_4$ was filtered out. Thereafter, the solvent was distilled off under reduced pressure. The mixture so obtained was separated and purified by silica gel column chromatography (developing solvent: hexane/ethyl acetate, 100/1, Rf=0.20). As a result, Targeted Compound (VIII) (177.7 mg, 0.45 mmol), which is a polycyclic fused ring type π-conjugated organic material of the present invention, was obtained in a 90% yield.

The properties of Targeted Compound (VIII) are as follows. $^1$H NMR (CDCl$_3$): δ 0.51 (s, 12H), 7.26 (m, 2H), 7.38 (t, J=7.6 Hz, 4H), 7.52 (m, 6H), 7.60 (s, 2H).

Example 9

In the following, a method for synthesizing 1,1,1',1'-Tetramethyl-bi(1H-1-silainden-2-yl) (IX) will be described with reference to Scheme 3 shown above.

A mixture of lithium (12 mg, 1.73 mmol) and naphthalene (222 mg, 1.73 mmol) was stirred in THF (2.5 mL) at room temperature for 4 hours. As a result, a lithium-naphthalenide solution was prepared. To the solution, a solution in which Intermediate (VI) (130 mg, 0.41 mmol) was mixed with THF (1 mL) was added at room temperature. Immediately after the reaction mixture had been stirred for 5 minutes, the reaction mixture was mixed with a saturated ammonium chloride solution.

Then, the reaction mixture was extracted with ether. The organic solvent layer so obtained was washed with saturated saline, and then was dried using anhydrous MgSO$_4$. Then, the anhydrous MgSO$_4$ was filtered out. Thereafter, the solvent was distilled off under reduced pressure. The mixture so obtained was separated and purified by silica gel column chromatography (developing solvent: hexane, Rf=0.24). As a result, Targeted Compound (IX) (45 mg, 0.14 mmol), which is a polycyclic fused ring type n-conjugated organic material of the present invention, was obtained in a 34% yield.

The properties of Targeted Compound (IX) are as follows. $^1$H NMR (CDCl$_3$): δ 0.47 (s, 12H), 7.12 (s, 2H), 7.25 (m, 6H), 7.52 (d, J=6.9 Hz, 2H).

All of the compounds so obtained exhibited good fluorescence properties. For example, in THF, Compounds (IX), (VIIa), and (VIII) exhibit absorption maximums at 364 nm, 375 nm, and 398 nm, respectively. Further, Compounds (IX), (VIIa), and (VIII) exhibit fluorescence properties at 417 nm, 437 nm, and 445 nm, respectively. Furthermore, Compounds (IX), (VIIa), and (VIII) have fluorescence quantum yields of 0.49 (anthracene), 0.86 (9,10-diphenylanthracene), and 0.73 (perylene), respectively. Note that the substances in the parentheses are standard substances used for calculating the fluorescence quantum yields.

Example 10

In the following, an example of the synthesis of Targeted Compound (VIIe) will be described with reference to Scheme 4 shown below. This is a typical example of the synthesis of a diol compound.

Scheme 4

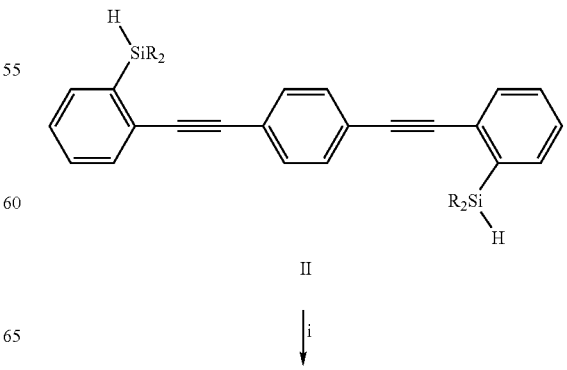

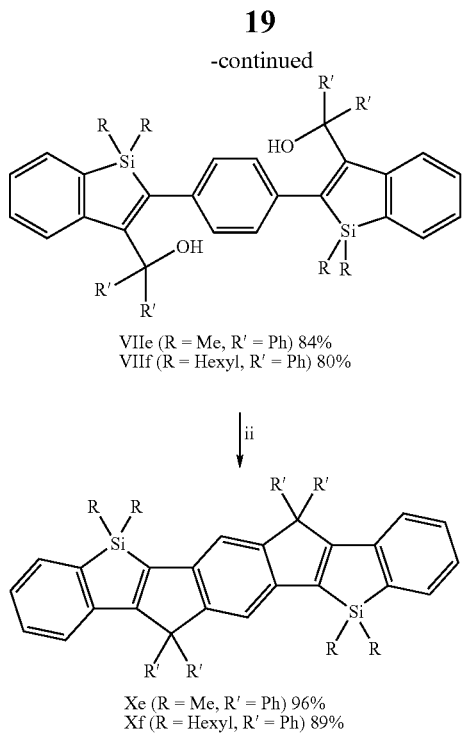

VIIe (R = Me, R' = Ph) 84%
VIIf (R = Hexyl, R' = Ph) 80%

↓ ii

Xe (R = Me, R' = Ph) 96%
Xf (R = Hexyl, R' = Ph) 89%

First, a mixture of lithium (22.7 mg, 3.26 mmol) and naphthalene (0.417 g, 3.26 mmol) was stirred in THF (2.5 mL) at room temperature for 4 hours. As a result, a lithium-naphthalenide solution was prepared. To the solution, a solution in which Compound (II) (0.300 g, 0.76 mmol) was mixed with THF (2 mL) was added at room temperature. Note that the molar quantity ratio of the mixture to Compound (II) is approximately 4:1. The reaction mixture was stirred for 5 minutes at room temperature. Thereafter, benzophenone (0.595 g, 3.26 mmol) was added to the reaction mixture, and then the reaction mixture was stirred for 10 minutes. Thereafter, a saturated ammonium chloride solution was added to the reaction mixture, and then the reaction mixture was extracted with ether.

The organic layer so obtained was washed with saturated saline, and then was dried using anhydrous MgSO$_4$. Then, the anhydrous MgSO$_4$ was filtered out. Thereafter, the solvent was distilled off under reduced pressure. The mixture so obtained was separated and purified by silica gel column chromatography (hexane/AcOEt 10/1, Rf=0.10). As a result, Targeted Compound (VIIe) (0.487 g, 0.64 mmol, 84% yield) was obtained in the form of a white solid.

The properties of Targeted Compound (VIIe) are as follows. Mp. 295-297° C. $^1$H NMR (270 MHz, CDCl$_3$). δ 0.28 (s, 12H), 2.99 (s, 2H), 6.53 (s, 4H), 6.90-7.12 (m, 6H), 7.19-7.23 (m, 12H), 7.32-7.36 (m, 8H), 7.52 (d, J=6.9 Hz, 2H). $^{13}$C NMR (67.8 MHz, CDCl$_3$): δ −4.53, 83.14, 125.63, 126.05, 127.38, 127.56, 127.99, 128.28, 129.09, 131.21, 137.48, 138.45, 145.68, 147.48, 149.62, 153.49. Elemental Anal. Cal. for C$_{52}$H$_{46}$O$_2$Si$_2$, C, 82.28; H, 6.11; Found; C, 82.10, H, 6.23.

Example 11

In the following, examples of the synthesis of other Targeted Compounds (VIIf, VIIIb, VIIIc, VIIId, XIII, XVI) will be described with reference to Scheme 4 shown above and Schemes 5 through 7 shown below. These are other examples of the synthesis of a diol compound.

Scheme 5

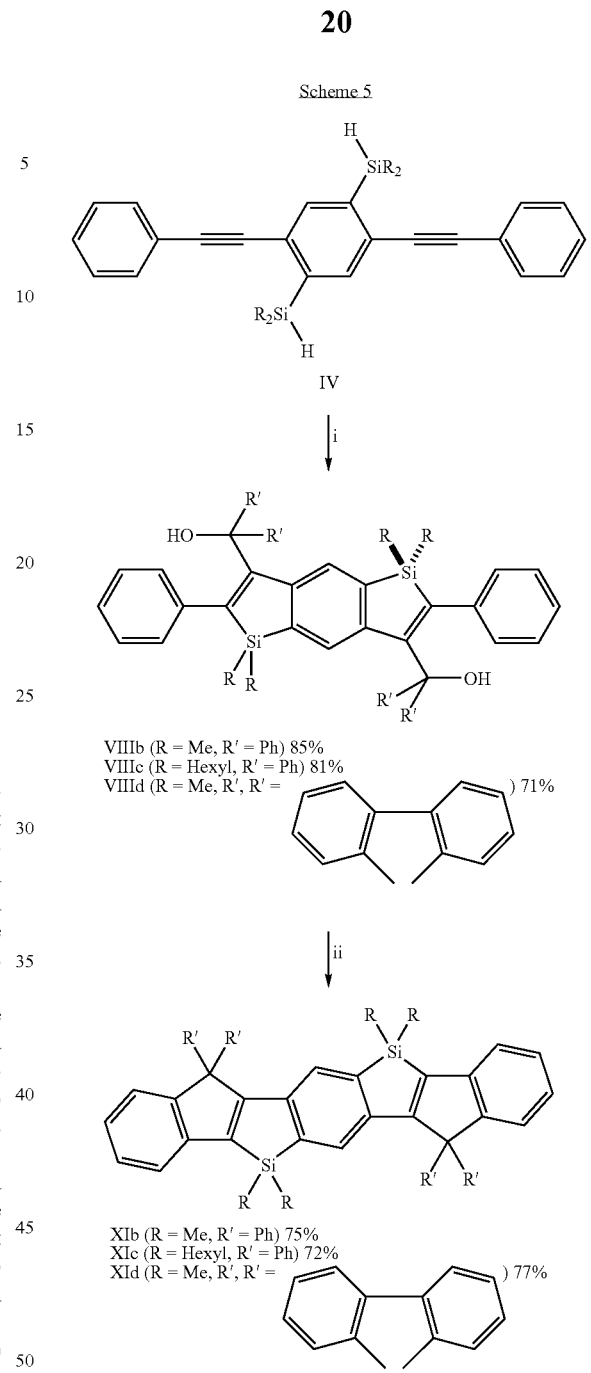

IV

↓ i

VIIIb (R = Me, R' = Ph) 85%
VIIIc (R = Hexyl, R' = Ph) 81%
VIIId (R = Me, R', R' = 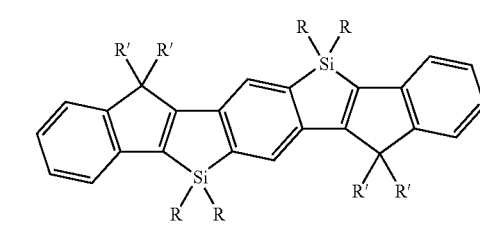 ) 71%

↓ ii

XIb (R = Me, R' = Ph) 75%
XIc (R = Hexyl, R' = Ph) 72%
XId (R = Me, R', R' = 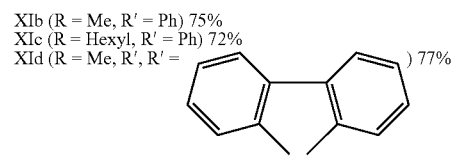 ) 77%

Scheme 6

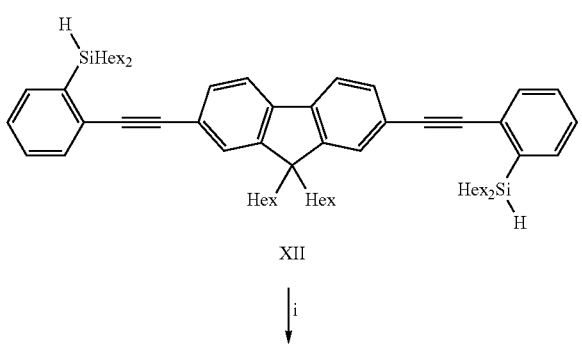

XII

↓ i

-continued

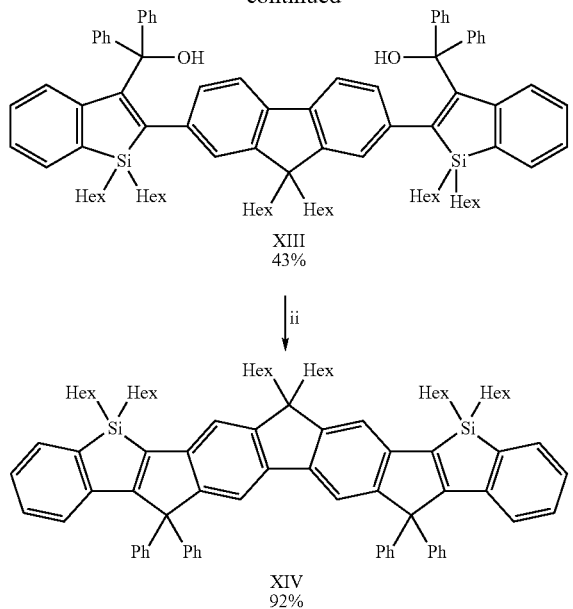

XIII
43%

↓ ii

XIV
92%

Scheme 7

XV

↓ i

XVI

↓ ii

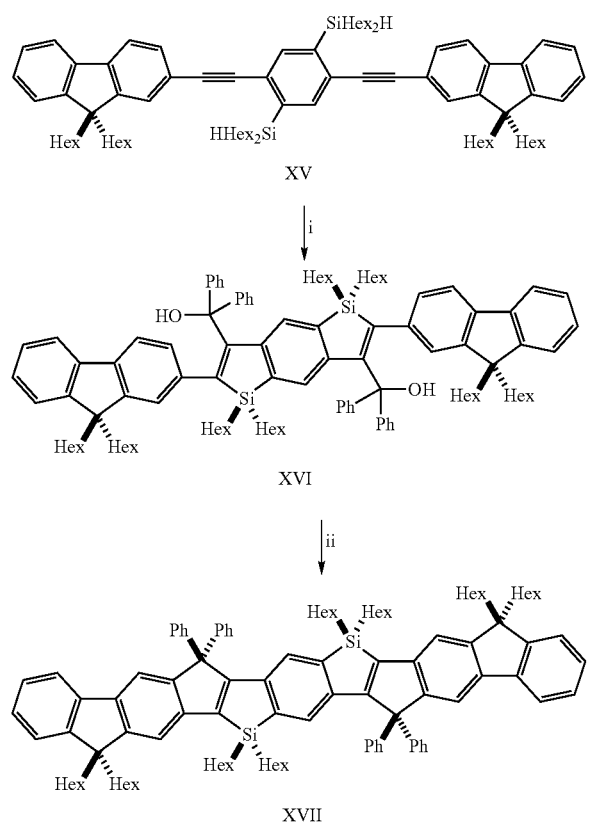

XVII

In the following, Targeted Compounds (VIIf, VIIIb, VIIIc, VIIId, XIII, XVI) were synthesized in the same manner as Targeted Compound (VIIe). The properties of each of those compounds are as follows.

Targeted Compound VIIf: 80% yield, yellow solid. $^1$H NMR (270 MHz, CDCl$_3$): δ 0.71-0.88 (m, 20H), 1.20-1.40 (m, 32H), 2.98 (s, 2H), 6.57 (s, 4H), 6.85 (d, J=8.1 Hz, 2H), 6.97 (t, J=7.6 Hz, 2H), 7.07 (t, J=7.0 Hz, 2H), 7.20-7.23 (m, 12H), 7.35-7.38 (m, 8H), 7.49 (d, J=6.8 Hz, 2H); $^{13}$C NMR (67.8 MHz, C$_6$D$_6$): δ 12.61, 15.13, 23.75, 24.89, 32.56, 34.25, 84.45, 126.59, 127.30, 128.46, 128.77, 129.12, 129.54, 130.09, 132.63, 137.93, 139.56, 146.80, 147.38, 151.81, 156.68.

Targeted Compound VIIb: 85% yield, white solid. $^1$H NMR (270 MHz, CDCl$_3$). δ 0.03 (s, 12H), 3.02 (s, 2H), 6.71 (d, J=6.9 Hz, 4H), 6.94 (s, 2H), 6.96-7.06 (m, 6H), 7.20-7.24 (m, 10H), 7.33-7.36 (m, 10H). $^{13}$C NMR (67.8 MHz, CDCl$_3$). δ −4.98, 83.23, 125.02, 126.17, 127.23, 127.79, 128.15, 128.31, 129.81, 139.49, 140.98, 145.97, 146.80, 147.50, 153.84.

Targeted Compound VIIIc: 81% yield, yellow solid. $^1$H NMR (400 MHz, C$_6$D$_6$): δ 0.70-0.85 (m, 8H), 0.91 (t, J=7.08), 1.20-1.28 (m, 32H), 3.14 (s, 2H), 6.81 (t, J=7.08, 2H), 6.92-7.13 (m, 20H), 7.53 (s, 2H), 7.63 (d, J=7.32, 8H). $^{13}$C NMR (67.8 MHz, C$_6$D$_6$). δ 12.20, 15.01, 23.58, 24.68, 32.51, 33.98, 84.60, 126.26, 127.25, 128.73, 129.30, 129.56, 132.18, 139.13, 143.02, 147.03, 147.74, 148.65, 157.13. Elemental Anal. Cal. for C$_{72}$H$_{86}$O$_2$Si$_2$, C, 83.18; H, 8.34; Found; C, 83.31, H, 8.30.

Targeted Compound VIId: 71% yield, yellow solid. $^1$H NMR (210 MHz, CD$_2$Cl$_2$). δ −0.13 (s, 12H), 6.23 (s, 2H), 7.18-7.24 (m, 10H), 7.30-7.40 (m, 12H), 7.72 (d, J=7.6 Hz, 4H). $^{13}$C NMR (100.4 MHz, CD$_2$Cl$_2$) δ −5.73, 86.54, 120.31, 123.93, 125.41, 125.86, 126.69, 128.36, 128.47, 129.33, 140.13, 140.27, 141.98, 144.39, 148.12, 148.36, 148.89. HRMS (EI): 754.2749 (M$^+$), Cal. For C$_{52}$H$_{42}$O$_2$Si$_2$+: 754.2723.

Targeted Compound XIII: 43% yield. $^1$H NMR (400 MHz, C$_6$D$_6$) 0.81 (t, J=6.8 Hz, 8H), 0.88 (t, J=6.8 Hz, 12H), 1.02 (t, J=8.0 Hz, 8H), 1.13-1.26 (m, 38H), 1.40-1.50 (m, 4H), 1.55-1.67 (m, 4H), 1.82 (br, 4H), 6.91 (t, J=8.0 Hz, 2H), 6.95 (t, J=7.2 Hz, 2H), 7.02-7.15 (m, 16H), 7.20 (d, J=8.0 Hz, 2H), 7.25 (d, J=8.0 Hz, 2H), 7.50 (d, J=6.8 Hz, 2H), 7.70 (d, J=7.6 Hz, 8H).

$^{13}$C NMR (67.8 MHz, C$_6$D$_6$): δ 12.58, 14.89, 14.96, 23.60, 24.84, 25.13, 31.00, 32.52, 32.80, 34.16, 37.92, 41.54, 55.78, 84.86, 120.90, 121.71, 126.21, 126.60, 128.84, 129.68, 130.17, 132.71, 137.94, 139.65, 141.74, 147.20, 151.82, 152.18, 157.74.

Example 12

In the following, an example of the synthesis of Targeted Compound Xe will be described with reference to Scheme 4. This is a typical example of the synthesis carried out by subjecting a diol compound to a cyclization reaction in which Lewis acid is used.

First, to a solution in which Compound VIIe (0.248 g, 0.330 mmol) was mixed with CH$_2$Cl$_2$ (35 mL), BF$_3$.OEt$_2$ (90 mL) was added at room temperature. The reaction mixture was stirred for 15 minutes. To the reaction mixture, water was added. Thereafter, the organic layer was extracted with ether. The organic solvent layer so obtained was washed with saturated saline, and then was dried using anhydrous MgSO$_4$. Then, the anhydrous MgSO$_4$ was filtered out. Thereafter, the solvent was distilled off under reduced pressure. The mixture so obtained was washed with hexane, and then was dried under reduced pressure. As a result, Targeted Compound Xe (0.226 g, 0.313 mmol, 96% yield) was obtained in the form of a yellow solid.

The properties of Targeted Compound Xe are as follows. $^1$H NMR (270 MHz, CDCl$_3$): δ 0.38 (s, 12H), 6.98-7.06 (m, 8H), 7.14-7.24 (m, 12H), 7.30-7.35 (m, 8H), 7.44 (m, 2H).

$^{13}$C NMR (67.8 MHz, CDCl$_3$): δ −3.83, 66.65, 118.13, 123.27, 125.94, 126.57, 128.10, 129.11, 129.20, 131.10, 142.05, 142.37, 142.42, 144.55, 145.72, 157.18, 170.25.

Example 13

In the following, Targeted Compounds Xf, XIb, XIc, XId, XIV, and XVII were synthesized in the same manner as Target Compound Xe (see Schemes 4 through 7). The properties of each of those compounds are as follows.

Targeted Compound Xf: 89% yield, yellow solid. $^1$H NMR (400 MHz, CDCl$_3$): δ 0.77-0.80 (m, 12H), 0.90-0.95 (m, 8H), 1.10-1.20 (m, 24H), 1.27-1.34 (m, 8H), 7.06 (m, 8H), 7.18-7.24 (m, 10H), 7.30-7.35 (m, 10H), 7.45 (m, 2H).

Targeted Compound XIb: 75% yield, yellow solid. Mp. 202-204° C. $^1$H NMR (400 MHz, CDCl$_3$): δ 0.34 (s, 12H), 7.06-7.10 (m, 2H), 7.16-7.25 (m, 16H), 7.30-7.33 (m, 12H). $^{13}$C NMR (100.4 MHz, CDCl$_3$): −4.28, 67.20, 121.86, 124.39, 125.58, 126.68, 127.08, 127.11, 128.07, 128.97, 142.41, 142.53, 143.75, 144.89, 157.49, 171.10.

Targeted Compound XIc: 72%, yellow solid. $^1$H NMR (400 MHz, CDCl$_3$): δ 0.76-0.90 (m, 20H), 1.08-1.30 (m, 32H), 7.07 (t, J=7.8 Hz, 2H), 7.16-7.24 (m, 16H), 7.26-7.35 (m, 12H). $^{13}$C NMR (100.4 MHz, CDCl$_3$): 11.71, 14.02, 22.49, 24.07, 31.33, 32.84, 67.07, 122.08, 124.24, 125.40, 126.58, 127.10, 127.92, 127.98, 128.94, 142.34, 143.81, 144.22, 157.59, 171.94. Elemental Anal. Cal. for C$_{72}$H$_{82}$Si$_2$, C, 86.17; H, 8.24; Found; C, 85.89, H, 8.19.

Targeted Compound XId: 77%, yellow solid. $^1$H NMR (400 MHz, CDCl$_3$): δ 0.21 (s, 12H), 6.08 (s, 2H), 6.61 (d, J=7.6 Hz, 2H), 0.76 (d, J=7.2 Hz, 4H), 6.92 (t, J=7.6 Hz, 2H), 7.06 (t, J=7.6 Hz, 4H), 7.21 (t, J=7.6 Hz, 2H), 7.34-7.38 (m, 6H), 7.89 (d, J=7.2 Hz, 4H).

Targeted Compound XIV: 92%, yellow solid. $^1$H NMR (270 MHz, CDCl$_3$): δ 0.74-0.82 (m, 18H), 1.04-1.28 (m, 36H), 1.38-1.44 (m, 8H), 1.97 (m, 4H), 7.0-7.1 (m, 6H), 7.17-7.34 (m, 22H), 7.43-7.48 (m, 4H).

Targeted Compound XVII: yellow solid. $^1$H NMR (270 MHz, CDCl$_3$): δ 0.70-0.75 (m, 32H), 0.89-0.95 (m, 8H), 1.00-1.21 (m, 48H), 1.32-1.37 (m, 8H), 1.92-1.98 (m, 8H), 7.18-7.28 (m, 22H), 7.32-7.36 (m, 8H), 7.53 (d, J=6.5 Hz, 2H), 7.61 (s, 2H).

FIG. 1 is a graph showing results of examining: (a) wavelengths at which (i) Targeted Compound Xe, (ii) Targeted Compound Xib, and (iii) Comparative Compound Comp., which is used for comparison with the two targeted compounds, exhibit absorption maximums, respectively; and (b) respective fluorescence properties of the three compounds.

Thank you for all your trouble. Please add Compounds (19) to (21) and XIX to XXI stored in the attached PDF file to the specification. The properties of each of Compounds XVIII to XX are as follows. Sorry to trouble you with last-minute notice. Thank you for your help.

Example 14

In the following, Targeted Compound XXI was synthesized in the same manner as Targeted Compound Xe, so as to be synthesized from Compound XIX, serving as a starting material, via Compound XX, serving as an intermediate (see Schemes 4 through 7).

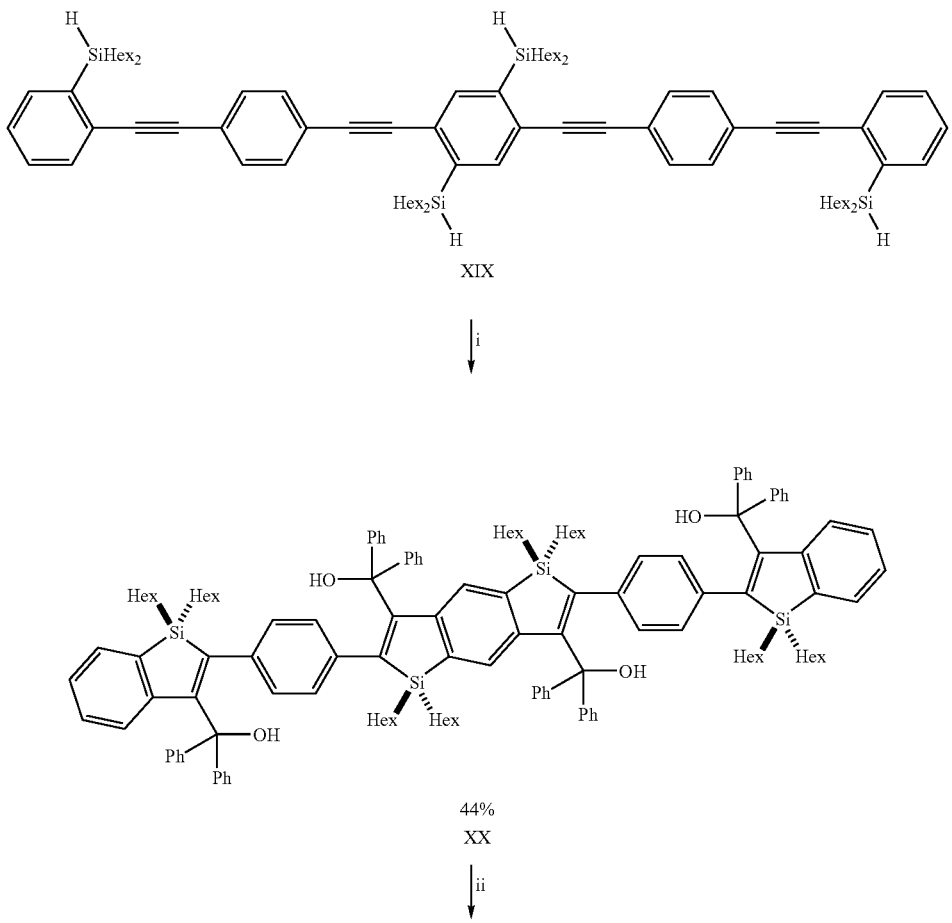

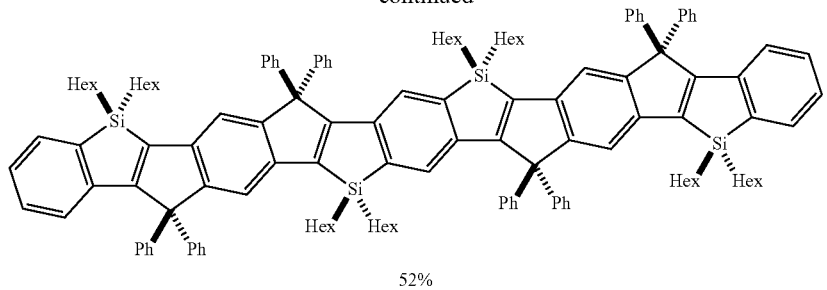

52%
XXI

Reagents and conditions: i, 1) LiNaph, THF, rt, 5 min; 2) Ph₂CO, rt, 15 min. ii, BF₃·OEt₂, CH₂Cl₂, 15 min.

The properties of each of Targeted Compounds XIX and XXI are as follows.

Compound XIX. 44% yield, Mp. 164-166° C. $^1$H NMR (400 MHz, CDCl$_3$): δ 81-0.94 (m, 36H), 1.14-1.36 (m, 68H), 2.97 (s, 2H), 3.13 (s, 2H), 6.76-6.81 (m, 8H), 6.88 (td, J=7.6 Hz, 1.2 Hz, 2H), 6.94 (td, J=7.0 Hz, 1.2 Hz, 2H), 7.00-7.15 (m, 24H), 7.30 (s, 2H), 7.31 (d, J=8.0 Hz), 7.46 (dd, J=7.0 Hz, 1.2 Hz), 7.55 (dd, J=8.0 Hz, 1.2 Hz, 8H), 7.62 (dd, J=8.0 Hz, 1.2 Hz, 8H). $^{13}$C NMR (100.4 MHz, CDCl$_3$): δ 12.35, 14.91, 15.01, 23.56, 23.60, 24.66, 32.36, 32.47, 34.02, 34.05, 84.22, 84.22, 126.60, 127.21, 127.44, 128.22, 128.27, 128.50, 128.74, 129.13, 129.19, 129.50, 130.10, 132.08, 132.64, 137.96, 139.08, 139.47, 139.88, 146.78, 147.00, 147.34, 147.86, 148.85, 151.76, 156.36, 157.25. HRMS (FAB): Calculated for C$_{138}$H$_{166}$O$_4$Si$_4$+: 1999.1863; found 1999.1893.

Compound XXI. 52% yield, Mp. 255-258° C. $^1$H NMR (400 MHz, CDCl$_3$): δ 0.73-0.80 (m, 32H), 0.90-0.94 (m, 8H), 1.06-1.18 (m, 56H), 1.26-1.34 (m, 8H), 7.01-7.06 (m, 6H), 7.14-7.22 (m, 28H), 7.30-7.33 (m, 18H), 7.44-7.46 (m, 2H). $^{13}$C NMR (100.4 MHz, CDCl$_3$): δ 11.63, 11.83, 14.04, 22.45, 22.47, 24.05, 24.16, 31.28, 31.35, 32.80, 32.94, 66.76, 118.16, 118.46, 123.23, 125.65, 126.46, 127.56, 127.88, 127.99, 129.07, 129.11, 132.39, 141.35, 141.98, 142.44, 142.64, 142.73, 142.96, 144.44, 145.16, 145.24, 156.96, 157.22, 170.62, 171.09. Anal. Cal for C$_{138}$H$_{158}$Si$_4$: C 85.92, H 8.26; found: C 85.41, H 8.29. HRMS (FAB): Calculated for C$_{138}$H$_{158}$Si$_4$: 1927.1441; found 1927.1466.

When the synthetic scheme under which Compound XIX is converted to Compound XXI is generalized, the following scheme under which Compound (19) is converted to Compound (21) is obtained. Note that R$^1$, R$^2$, R$^6$, R$^7$, and X shown in chemical formulas respectively representing Compounds (19) through (21) are the same as those described above.

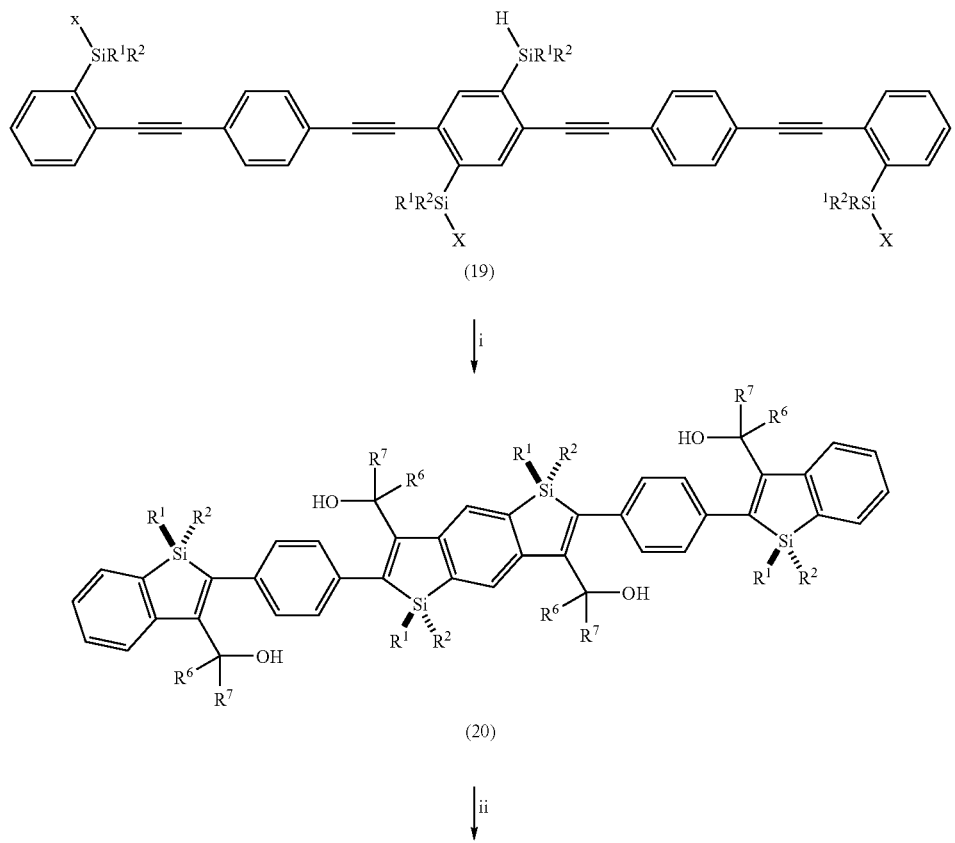

-continued

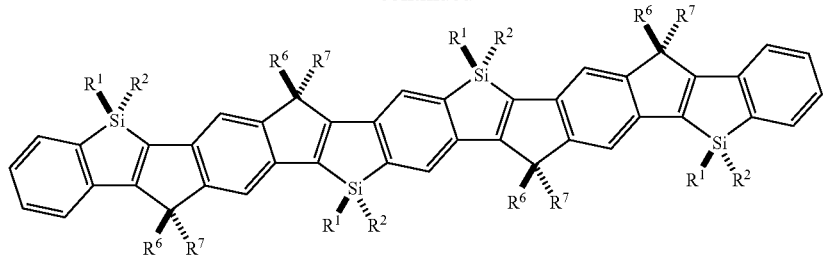

(21)

Reagents and conditions: i, 1) LiNaph, THF, rt, 5 min; 2) ketone, rt, 15 min. ii, BF₃·OEt₂, CH₂Cl₂, 15 min.

INDUSTRIAL APPLICABILITY

A polycyclic fused ring type π-conjugated organic material according to the present invention is a novel compound which can be applied to a light-emitting material and a charge-transporting material. Further, the polycyclic fused ring type π-conjugated organic material exhibits highly efficient light-emitting and charge-transporting properties, and therefore can be applied to a field such as EL. Further, an intermediate according to the present invention for synthesis of the polycyclic fused ring type π-conjugated organic material and a method according to the present invention for producing the polycyclic fused ring type n-conjugated organic material can be suitably used for producing the polycyclic fused ring type π-conjugated organic material.

The invention claimed is:

1. A polycyclic fused ring type π-conjugated organic material having a structure represented by following formula (3):

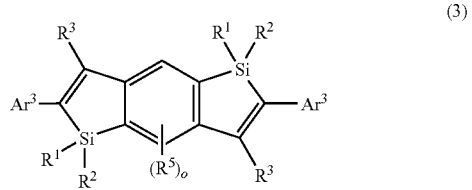

(3)

where $Ar^3$ is an aryl group, a substituted aryl group, a bivalent oligoarylene group, a bivalent substituted oligoarylene group, a monovalent heterocyclic group, a monovalent substituted heterocyclic group, a monovalent oligoheterocyclic group, or a monovalent substituted oligoheterocyclic group; $R^1$ and $R^2$ are independently a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amio group, a substituted amino group, a silyl group, a substituted silyl group, a silyloxy group, a substituted silyloxy group, an arylsulfonyloxy group, an alkylsulfonyloxy group, a monovalent heterocyclic group, or a halogen atom; $R^3$ is a hydrogen group, an alkyl group, an alkylthio group, an aryl group, an arylthio group, an arylalkyl group, an arylalkylthio group, an arylalkenyl group, an arylalkynyl group, an allyl group, a hydroxyalkyl group, a hydroxymethyl group, a substituted hydroxymethyl group, a silyl group, a substituted silyl group, a stannyl group, a substituted stannyl group, magnesium halide, zinc halide, boronic acid, boronic ester, a boryl group, a monovalent heterocyclic group, or a halogen atom; $R^5$ is a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amio group, a substituted amino group, a silyl group, a substituted silyl group, a silyloxy group, a substituted silyloxy group, an arylsulfonyloxy group, an alkylsulfonyloxy group, a substituted boryl group, a monovalent heterocyclic group, or a halogen atom; and o is an integer of 2.

2. A polycyclic fused ring type π-conjugated organic material having a structure represented by following formula (4):

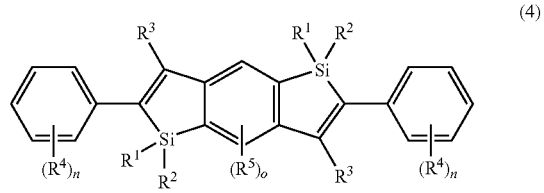

(4)

where $R^1$ and $R^2$ are independently a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amio group, a substituted amino group, a silyl group, a substituted silyl group, a silyloxy group, a substituted silyloxy group, an arylsulfonyloxy group, an alkylsulfonyloxy group, a monovalent heterocyclic group, or a halogen atom; $R^3$ is a hydrogen group, an alkyl group, an alkylthio group, an aryl group, an arylthio group, an arylalkyl group, an arylalkylthio group, an arylalkenyl group, an arylalkynyl group, an allyl group, a hydroxyalkyl group, a hydroxymethyl group, a substituted hydroxymethyl group, a silyl group, a substituted silyl group, a stannyl group, a substituted stannyl group, magnesium halide, zinc halide, boronic acid, boronic ester, a boryl group, a monovalent heterocyclic group, or a halogen atom; $R^4$ and $R^5$ are independently a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amio group, a substituted amino group, a silyl group, a substituted silyl group, a silyloxy group, a substituted silyloxy group, an arylsulfonyloxy group, an alkylsulfonyloxy group, a substituted boryl group, a monovalent heterocyclic group, or a halogen atom; n is an integer of 0 to 5; and o is an integer of 2.

3. A polycyclic fused ring type π-conjugated organic material having a structure represented by following formula (17):

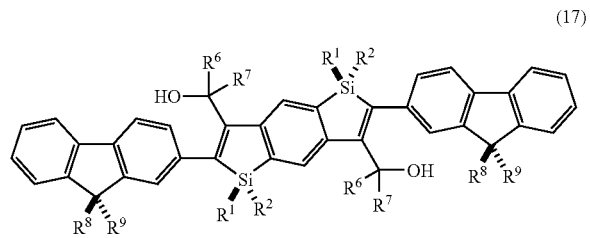

(17)

where $R^1$ and $R^2$ are independently a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an allyl group, an amio group, a substituted amino group, a silyl group, a substituted silyl group, a silyloxy group, a substituted silyloxy group, an arylsulfonyloxy group, an alkylsulfonyloxy group, a monovalent heterocyclic group, or a halogen atom; $R^6$ and $R^7$ are either (i) independently a hydrogen atom, an alkyl group, an aryl group, a substituted aryl group, a monovalent heterocyclic group, a monovalent substituted heterocyclic group, an alkoxy group, an aryloxy group, an arylalkyl group, an arylalkoxy group, an arylalkenyl group, an arylalkynyl group, or an allyl group, or (ii) mutually a bivalent biaryl group; and $R^8$ and $R^9$ are either (a) independently a hydrogen atom, an alkyl group, an alkoxy group, an alkylthio group, an aryl group, a substituted aryl group, an arylalkyl group, an arylalkenyl group, an arylalkynyl group, an allyl group, a silyl group, a substituted silyl group, an acyl group, or a monovalent heterocyclic group, or (b) mutually a bivalent biaryl group.

* * * * *